(12) United States Patent
Karpov

(10) Patent No.: US 6,696,048 B2
(45) Date of Patent: Feb. 24, 2004

(54) SUNSCREEN COMPOSITION

(75) Inventor: Inna Karpov, Germantown, TN (US)

(73) Assignee: Schering-Plough Healthcare Products, Inc., Memphis, TN (US)

( * ) Notice: Subject to any disclaimer, the term of this patent is extended or adjusted under 35 U.S.C. 154(b) by 132 days.

(21) Appl. No.: 10/028,585

(22) Filed: Dec. 20, 2001

(65) Prior Publication Data

US 2003/0118524 A1 Jun. 26, 2003

(51) Int. Cl.$^7$ .............................. A61K 7/42; A61K 7/44; A61K 7/00
(52) U.S. Cl. ........................... 424/59; 424/60; 424/400; 424/401; 514/937; 514/939
(58) Field of Search .............................. 424/59, 60, 400, 424/401; 514/937, 939

(56) References Cited

U.S. PATENT DOCUMENTS

| 5,571,503 | A | | 11/1996 | Mausner | 424/59 |
| 5,902,591 | A | * | 5/1999 | Herstein | 424/401 |
| 6,217,876 | B1 | | 4/2001 | Pauly | 424/195.1 |

FOREIGN PATENT DOCUMENTS

| WO | WO 99/20250 | 4/1999 |

* cited by examiner

*Primary Examiner*—Shelley A. Dodson
(74) *Attorney, Agent, or Firm*—Robert A. Franks

(57) ABSTRACT

Described is a method for preparing sunscreening compositions that contain chlorphenesin as a biocidal preservative, wherein the chlorphenesin is dissolved in water-insoluble components.

12 Claims, No Drawings

SUNSCREEN COMPOSITION

This invention relates to sunscreening compositions for application to the skin, and more particularly to sunscreen products which are protected against microbial proliferation using the biocide chlorphenesin.

Sunscreening compositions are increasingly being considered as essential protectants for persons spending significant amounts of time in outdoor areas during daylight hours. The incidence of skin damage from actinic solar radiation, including skin aging, solar keratoses and various types of cancerous lesions is quite high, and it is generally recognized that many of these conditions have their origins in exposure to ultraviolet wavelength radiation.

Many sunscreen products are emulsions such as lotions and creams, either of the oil-in-water type or the water-in-oil type. Such systems can be subject to microbial proliferation during storage and use, the microorganisms being introduced from the environment, container or ingredients during manufacture or from the environment during use, as the container is repeatedly opened and closed.

Other commercial products are sunscreen oils, preferred by some consumers over the more common emulsion products. These also are subject to microbial contamination during manufacture and use. Therefore, it is customary to include one or more biocidal ingredients in the compositions to avoid problems such as product viscosity changes, pH changes, emulsion breakdown, visible microorganism growth, color changes, disagreeable odor formation and user skin reactions that may be caused by microbes.

A biocide, sometimes referred to as a "preservative" or "antimicrobial," component of a product should ideally have a broad spectrum of activity, since the product could be exposed to many different classes of bacteria, yeast, mold and other types of contaminants. As microorganisms usually require water for their existence and proliferation, biocides are typically chosen to be soluble in the aqueous phase of an emulsion; sometimes, a biocide having water solubility below its biocidal-effective concentration can be dissolved in a cosolvent, and the resulting solution added to the aqueous phase for preparing an emulsion.

Chlorphenesin, having the chemical name 3-(4-Chlorophenoxy)-1,2-propanediol and the formula $C_9H_{11}ClO_3$, is a broad-spectrum biocide that has been used in cosmetic-type products. It has a very low water solubility and commonly is dissolved in cosolvents, including alcohol, diol and triol cosolvents (collectively referred to hereinafter as "alcohols") having a high water solubility, such as ethanol, phenoxyethanol, glycerin, propylene glycol, butylene glycol and others. When so dissolved, biocidal-effective amounts of chlorphenesin can then be solubilized in the aqueous phase of an emulsion product. However, this extra step of dissolution in the cosolvent is not convenient and adds to the manufacturing cost and complexity of the product, including requirements for raw material storage and documentation. Further, such cosolvent ingredients may add undesired properties to a particular product or may not be compatible with other desired ingredients.

SUMMARY OF THE INVENTION

The present invention includes a method for preparing sunscreen products that contain chlorphenesin, wherein the chlorphenesin is added directly to the water-insoluble 'oil' phase components before an emulsion is formed. The invention also includes sunscreen products that do not contain water as an ingredient, i.e., sunscreen oils, wherein chlorphenesin is added as a preservative component. Typically, the chlorphenesin is added to a water-insoluble mixture that contains the organic sunscreen active ingredients.

The invention further includes sunscreening emulsion compositions that are prepared to at least initially contain chlorphenesin in the water-insoluble phase.

Also encompassed by the invention is a sunscreen composition containing chlorphenesin, having a substantial absence of alcohol cosolvents (as discussed below) for the chlorphenesin.

DETAILED DESCRIPTION

The preparation of sunscreen emulsions for skin application is generally well known, and typically involves generating an "aqueous phase" by: combining water and water-soluble or water-dispersable ingredients to preferably, but not necessarily, form a solution; generating an "oil phase" by combining water-insoluble ingredients to preferably, but not necessarily, form a solution; then combining the aqueous and oil phases, usually under shearing conditions created by stirring or simultaneously passing the phases through a pumping device. If ingredients which are not soluble in either phase (such as particulate inorganic materials) are to be included in a product, they usually are dispersed in the phase where they will form the more stable dispersion, before the phases are combined. Many permutations of this general process are known, including the use of elevated temperatures for one or both phases, and the present invention is not to be restricted to any particular preparative method.

The resulting emulsions, commonly in the form of lotions or creams, are dispersions of fine droplets of one phase in a more or less continuous body of the other phase. Ingredients which are not soluble in either phase usually have an affinity for one of the phases, preferably the phase which is considered to be the "internal" phase. Formation and stability of the emulsion are enhanced by the inclusion of ingredients having surfactant properties; such components are known as emulsifiers and emulsion stabilizers. Numerous useful emulsifiers are listed at pages 1795–1803 in Volume 2 of J. A. Wenninger et al., *International Cosmetic Ingredient Dictionary and Handbook*, Eighth Edition, The Cosmetic, Toiletry, and Fragrance Association, Washington, D.C., 2000 (hereinafter referred to as "the CTFA book"). Many useful emulsion stabilizers are listed at pages 1742–1743 of that same book. Those skilled in the art of emulsion product preparation are fully aware of the considerations in selecting suitable emulsification ingredients for forming a stable emulsion system.

In addition to emulsion products, sunscreen oils are also popular with many consumers. These products do not have water as an added component, but may contain some moisture as an impurity in one or more of the ingredients. Generally, any water will be present in the oil products in very small concentrations; these products are considered to be substantially free of water.

Sunscreen compositions of the invention contain one or more organic sunscreen active ingredients. Those active ingredients which are presently approved by regulatory agencies in the United States include: Dioxybenzone, Oxybenzone, Sulisobenzone, Avobenzone, Cinoxate, Diethanolamine methoxycinnamate, Digalloyl trioleate, Ethyl 4-[bis(hydroxypropyl)] aminobenzoate, Padimate O, Octyl methoxycinnamate, Octyl salicylate, Glyceryl aminobenzoate, Homosalate, Menthyl anthranilate, Octocrylene, Aminobenzoic acid, Phenylbenzimidazole sulfonic acid and Trolamine salicylate. There are other active ingredients that have been accepted for use in other countries and several additional ingredients have been proposed for acceptance. All such active ingredients are considered to be useful in the present invention.

Chlorphenesin will not necessarily be the sole biocidal preservative in the sunscreening compositions of the invention. Other components having the same function, including those listed at pages 1765–1766 in the CTFA book, Volume 2, may be included in the compositions as needed.

Sunscreening products frequently contain other components, many of which impart cosmetic elegance to the composition. These components include emollients, humectants and other skin-conditioning agents, film formers, fragrances, agents affecting viscosity, colorants, pH adjusters and buffers, skin protectants and others. Many useful components are described in the volumes of the CTFA book, and their selection and amounts for a particular product are well within the ordinary skill in the art.

To prepare the products of the invention, the chlorphenesin biocide is included as a component of a water-insoluble phase. Chlorphenesin powder typically will be added to a solution or dispersion that includes the organic sunscreen active ingredients and may be among the later added ingredients for the oil phase, since it is a minor concentration component and can be dispersed more easily if added to a large amount of other ingredients. In many procedures, the combinations constituting the oil and/or aqueous phases will have been heated to facilitate solubilities of certain components, or to enhance emulsion formation when the phases are combined, and chemical stability of the chlorphenesin will be enhanced by cooling the oil phase combination to less than about 65° C. before the chlorphenesin is added and then avoiding any subsequent heating of the mixture to higher temperatures. The final sunscreen product usually will contain about 0.1 to about 1 percent by weight chlorphenesin; a more typical amount for a sunscreen product is about 0.1 to about 0.3 percent by weight.

After an emulsion product has been formed, a certain amount of the chlorphenesin can migrate to the aqueous phase and effectively control microbial concentrations in that phase. However, it is a characteristic of the invention that all of the chlorphenesin will have been initially introduced into the emulsion product as a component of the oil phase. Further, it is a feature of the invention that the chlorphenesin will not be dissolved in any solvent before it is added to the oil phase mixture.

The invention will be further illustrated by the following examples of sunscreen product compositions, where concentrations are weight percentages and, where possible, the names of the components are taken from the CTFA book. It is not intended that these examples will limit the scope of the invention, as established solely by the appended claims.

EXAMPLE 1

The components listed below are combined to form a sunscreen lotion product having an SPF value of 25:

| Part | Ingredient | Wt. percent |
|---|---|---|
| A | Water | 64.4978 |
|  | Carbomer | 0.12 |
| B | Sorbitol, 70% aqueous solution | 5 |
|  | Actiplex 185* | 0.01 |
|  | Disodium EDTA | 0.01 |

-continued

| Part | Ingredient | Wt. percent |
|---|---|---|
|  | Dye mixture | 0.0022 |
|  | Triethanolamine | 1.11 |
| C | Vitamin E | 0.05 |
|  | Octadecene/maleic anhydride copolymer | 0.8 |
|  | Stearic acid | 0.8 |
|  | Polyglyceryl-3 distearate | 0.6 |
|  | Sorbitan isostearate | 1.5 |
|  | Homosalate | 12 |
|  | Benzophenone-3 | 2 |
|  | Octyl salicylate | 5 |
|  | Propylparaben | 0.1 |
|  | Dimethicone | 0.4 |
|  | PVP/eicosene copolymer | 0.7 |
|  | Avobenzone | 2 |
|  | Octocrylene | 2 |
|  | Chlorphenesin | 0.3 |
| D | Fragrance | 0.5 |
|  | Benzyl alcohol | 0.5 |
| E | Water | q.s. |

*Actiplex 185 ™ is a mixture of butylene glycol, water, aloe barbadensis extract, matricaria extract, coneflower extract, quillaja saponaria extract and witch hazel extract, and is sold by Active Organics, Lewisville, Texas U.S.A.

To prepare the lotion, the Part A components are mixed until clear and smooth, then the Part B components are added and the mixture is heated to about 80° C. to form an aqueous phase solution. The components of Part C, except for the copolymer, chlorphenesin and dimethicone, are mixed together and heated to about 80° to form a solution, the copolymer is slowly added and mixed to dissolve, the temperature is decreased to about 63° C. and then the chlorphenesin is added and dissolved, and finally the dimethicone is added to complete an oil phase. With continuous mixing, the hot oil phase is added to the hot aqueous phase and the emulsion is allowed to cool to about 49° C., at which point the Part D components are added. Stirring is continued as the emulsion cools to ambient temperature, and then sufficient water (Part E) is added to compensate for the evaporative losses occurring during the procedure.

This lotion exhibits a commercially acceptable inhibition of microbial proliferation for at least one year.

EXAMPLE 2

The preparation of the preceding example is repeated, but reducing the water to 64.2978 percent and including 0.2 percent of methylparaben as an additional Part B component. This lotion exhibits a commercially acceptable inhibition of microbial proliferation for at least one year.

EXAMPLE 3

The components listed below are combined to form a sunscreen lotion product having an SPF value of 15:

| Part | Ingredient | Wt. percent |
|---|---|---|
| A | Water | 74.0978 |
|  | PEG-8 | 5 |
|  | Acrylates/C10–30 alkyl acrylate crosspolymer | 0.3 |
|  | Dye mixture | 0.0022 |
|  | Actiplex 185 | 0.1 |
|  | Disodium EDTA | 0.01 |
| B | Octocrylene | 4 |
|  | Octyl salicylate | 5 |

-continued

| Part | Ingredient | Wt. percent |
|---|---|---|
|  | PVP/eicosene copolymer | 2 |
|  | Vitamin A palmitate | 0.2 |
|  | Propylparaben | 0.1 |
|  | Methylparaben | 0.2 |
|  | Avobenzone | 2 |
|  | Chlorphenesin | 0.15 |
|  | Homosalate | 5 |
| C | Fragrance | 0.5 |
|  | Benzyl alcohol | 0.5 |
| D | Triethanolamine | 0.34 |
|  | Water | 0.5 |
| E | Water | q.s. |

To prepare the lotion, the water of Part A is charged to a vessel equipped with a stirrer and the acrylates/C10–30 alkyl acrylate crosspolymer is dispersed in the water with vigorous stirring to form a smooth dispersion, then the remaining Part A ingredients are added and mixed. In a separate vessel, the Part B ingredients, except for chlorphenesin, are combined with stirring and then the mixture is heated to about 60–65° C. to dissolve the PVP/eicosene copolymer, after which the chlorphenesin is added. With vigorous mixing, the Part B mixture is added to the Part A mixture and then the Part C ingredients are added. The Part D components are combined to form a solution and then mixed into the combination of Parts A, B and C ingredients. Stirring is continued as the product cools to room temperature, and the water of Part E is added to compensate for the evaporation losses occurring during the preparation.

This lotion exhibits a commercially acceptable inhibition of microbial proliferation for at least one year.

EXAMPLE 4

A sunscreen oil composition having an SPF value of 15 is prepared using the following components:

| Part | Ingredient | Wt. percent |
|---|---|---|
| A | Caprylic/capric triglyceride | 37 |
|  | Chlorphenesin | 0.1 |
|  | Octyl methoxycinnamate | 6 |
|  | Homomenthyl salicylate | 10 |
|  | Avobenzone | 2 |
| B | Vitamin E | 0.05 |
|  | Aloe vera lipoquinone | 0.1 |
|  | Light mineral oil | 4.25 |
|  | Isopropyl myristate | 30.2 |
| C | Fragrance | 0.3 |
|  | SD-40-2 denatured alcohol | 10 |

To prepare the product, the ingredients of Part A are combined and heated to about 60–65° C., with stirring. The ingredients of Part B are combined, with stirring, and are then added to the Part A combination. Ingredients of Part C are then added and stirring is continued as the product cools to room temperature.

This lotion exhibits a commercially acceptable inhibition of microbial proliferation for at least one year.

EXAMPLE 5

A sunscreen oil composition having an SPF value of 15 is prepared using the following components:

| Part | Ingredient | Wt. percent |
|---|---|---|
| A | Isopropyl myristate | 15 |
|  | Chlorphenesin | 0.3 |
|  | Octyl methoxycinnamate | 6 |
|  | Homomenthyl salicylate | 10 |
|  | Avobenzone | 2 |
| B | Vitamin E | 0.05 |
|  | Aloe vera lipoquinone | 0.1 |
|  | Light mineral oil | 66.25 |
| C | Fragrance | 0.3 |

To prepare the product, the ingredients of Part A are combined and heated to about 60–65° C., with stirring. The ingredients of Part B are combined, with stirring, and are added to the Part A combination. Then the ingredient of Part C is added and stirring is continued as the product cools to room temperature.

This lotion exhibits a commercially acceptable inhibition of microbial proliferation for at least one year.

What is claimed is:

1. A method for preparing a sunscreen composition containing chlorphenesin as a biocide, comprising the step of including the chlorphenesin in a combination of water-insoluble organic ingredients, wherein the composition is substantially free of alcohol solvents for chlorphenesin.

2. The method of claim 1, wherein the chlorphenesin is added directly to, and dissolved in, water-insoluble organic ingredients.

3. The method of claim 1, wherein the chlorphenesin is added to a water-insoluble mixture that contains one or more organic sunscreen active ingredients.

4. The method of claim 1, further comprising the steps of:
preparing a combination of water-soluble components; and mixing the water-insoluble and water-soluble combinations to form an emulsion product.

5. A sunscreen composition containing chlorphenesin as a biocide, which composition at least initially contains the chlorphenesin in a water-insoluble mixture and wherein the composition is substantially free of alcohol solvents for chlorphenesin.

6. The composition of claim 5, wherein the chlorphenesin is initially present in a water-insoluble mixture that contains organic sunscreen ingredients.

7. The composition of claim 5, wherein chlorphenesin comprises about 0.1 to about 1 percent by weight.

8. The composition of claim 5, wherein chlorphenesin comprises about 0.1 to about 0.3 weight percent.

9. The composition of claim 5, which is an emulsion.

10. The composition of claim 5, which is substantially free of water.

11. A sunscreen emulsion composition prepared by a process comprising combining a mixture of water-soluble ingredients with a combination of water-insoluble ingredients having chlorphenesin dissolved therein, and wherein the composition is substantially free of alcohol solvents for chlorphenesin.

12. A sunscreen oil composition having chlorphenesin dissolved therein, and which is substantially free of water and alcohol solvents for chlorphenesin.

* * * * *